(12) United States Patent
Cannell et al.

(10) Patent No.: US 6,861,077 B1
(45) Date of Patent: Mar. 1, 2005

(54) USE OF PLANT EXTRACTS IN A COSMETIC COMPOSITION TO PROTECT KERATINOUS FIBERS

(75) Inventors: David W. Cannell, Plainfield, NJ (US); Natalya Fadeeva, Clark, NJ (US); Hitendra Mathur, Woodbridge, NJ (US); Nghi Van Nguyen, Edison, NJ (US)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/576,800

(22) Filed: May 23, 2000

Related U.S. Application Data

(63) Continuation-in-part of application No. 09/527,599, filed on Mar. 17, 2000.

(51) Int. Cl.$^7$ ............................ A61K 35/78; A61K 7/06
(52) U.S. Cl. ........................ 424/725; 424/70.1; 424/74
(58) Field of Search ................................ 424/725, 70.1, 424/74, 70.2, 70.6, 70.9, 750, 757, 401, 70.13

(56) References Cited

U.S. PATENT DOCUMENTS

| | | | |
|---|---|---|---|
| 285,045 A | * | 9/1883 | Leip |
| 4,217,341 A | | 8/1980 | Suddick et al. |
| 4,297,374 A | | 10/1981 | Wess |
| 4,298,622 A | * | 11/1981 | Singh et al. ............... 426/254 |
| 4,518,517 A | | 5/1985 | Eigen et al. |
| 4,722,843 A | | 2/1988 | Vinson |
| 4,839,168 A | | 6/1989 | Abe et al. |
| 4,849,214 A | * | 7/1989 | Ruiseco |
| 5,053,222 A | | 10/1991 | Takasu et al. |
| 5,362,480 A | | 11/1994 | Au et al. |
| 5,409,902 A | | 4/1995 | Carson et al. |
| 5,416,075 A | * | 5/1995 | Carson et al. |
| 5,443,855 A | * | 8/1995 | Wolf et al. |
| 5,510,120 A | | 4/1996 | Jones et al. |
| 5,547,997 A | | 8/1996 | Kludas |
| 5,607,679 A | | 3/1997 | Rhodes |
| 5,624,672 A | * | 4/1997 | Bathurst et al. |
| 5,629,015 A | | 5/1997 | Ribier et al. |
| 5,665,342 A | * | 9/1997 | Salinas |
| 5,695,748 A | | 12/1997 | Francis |
| 5,739,102 A | | 4/1998 | Batterbury et al. |
| 5,747,050 A | * | 5/1998 | Tolpa |
| 5,788,954 A | | 8/1998 | Bonda et al. |
| 5,932,230 A | | 8/1999 | DeGrate |
| 5,935,596 A | | 8/1999 | Crotty et al. |
| 5,985,300 A | | 11/1999 | Crotty et al. |
| 6,124,362 A | * | 9/2000 | Bradbury et al. |
| 6,296,856 B1 | * | 10/2001 | Pineau et al. ............... 424/401 |

FOREIGN PATENT DOCUMENTS

| | | | | |
|---|---|---|---|---|
| DE | 27 03 189 A | | 8/1978 | |
| DE | 3901286 A1 | | 7/1990 | |
| DE | 00390128 | * | 7/1991 | |
| DE | 198 10 120 C1 | | 5/1999 | |
| DE | 019810120 C1 | * | 5/1999 | |
| DE | 19810120 | * | 5/1999 | |
| DE | 019810120 | * | 5/1999 | |
| EP | 0 243 019 | | 9/1987 | |
| EP | 0 315 541 A1 | | 5/1989 | |
| EP | 0 469 232 A1 | | 2/1992 | |
| EP | 0 668 072 A | | 8/1995 | |
| EP | 0 668 072 A1 | | 8/1995 | |
| EP | 0 481 701 B1 | | 10/1995 | |
| EP | 0 681 826 A2 | | 11/1995 | |
| EP | 0 699 689 A1 | | 6/1996 | |
| EP | 0 965 328 A1 | | 12/1999 | |
| FR | 2 694 018 | | 1/1994 | |
| FR | 2 694 021 | | 1/1994 | |
| FR | 2 740 331 | | 4/1997 | |
| FR | 2 740 331 A | | 4/1997 | |
| GB | 2 159 053 A | | 11/1985 | |
| JP | 59-101414 | | 6/1984 | |
| JP | 62-99319 | | 5/1987 | |
| JP | 62099319 | * | 5/1987 | |
| JP | 01190622 | * | 7/1989 | |
| JP | 3-148210 | | 6/1991 | |
| JP | 03284615 | * | 12/1991 | |
| JP | 403284615 | * | 12/1991 | |
| JP | 7-25762 | | 1/1995 | |
| JP | 07082119 | * | 3/1995 | |
| JP | 10-279439 | | 10/1998 | |
| JP | 11-49652 | | 2/1999 | |
| JP | 2000297011 A | * | 10/2000 | ............ A61K/7/00 |
| RO | 108529 B1 | * | 6/1994 | |
| WO | WO 97/05887 | | 2/1997 | |
| WO | WO 98/42303 | | 10/1998 | |
| WO | WO 99/40896 | | 8/1999 | |
| WO | WO 99 60989 A | | 12/1999 | |

OTHER PUBLICATIONS

Product Alert (Sep. 1992), pp. N/A. Freeman Botanical Humectant Plus Intensive Reconstructor; Infusion Hair Treatment; Replenshing Hot Oil Conditioning Treatment.*

Product Alert (Feb. 1995), pp. N/A. Clairol Herbal Essences Shampoo—Replenisher for Colored/Permed Very Dry/Damaged Hair; Refresher Clarifing for Normal to Oily Hair/Residue Removal; Reviver Ex.*

PTO 04–0900, Translation of foreign patent DE 019810120, Use of a Hair Treatment Product [Verwendung eines Mittels zur Haarbehandlung].*

(List continued on next page.)

Primary Examiner—Michele Flood
(74) Attorney, Agent, or Firm—Finnegan, Henderson, Farabow, Garrett & Dunner, L.L.P.

(57) ABSTRACT

The invention provides a method of protecting keratinous fiber from extrinsic damage, e.g., protein loss caused by exposure to heat, chemicals, etc., comprising the application of a composition comprising at least one plant extract. The invention also contemplates a method of improving combability and/or a method of improving curl formation of keratinous fibers. In another embodiment, the invention is drawn to a composition for the treatment or protection of keratinous fiber comprising willowherb extract.

13 Claims, 3 Drawing Sheets

OTHER PUBLICATIONS

Product Alert, (1/271997); Fredric Fekkai Shampoo du jour: Techniciam Shampoo; Instant Detangler; Technician Conditioner Manufacturer: Fredric Fekkai Beaute Category: Shampoos, Cream Rines & Conditioners.*
Popularity of Polyphenois Keeps Rising, *Cosmetics & Toiletries*, vol. 115, No. 3, p. 10 (2000).
Derwent Abstract of WO 99/40896.
Derwent Abstract of DE 19810120 C.
Derwent Abstract of JP 10279439 A.
Derwent Abstract of FR 2740331 A.
Derwent Abstract of JP 7025762 A.
Derwent Abstract of FR 2694021.
Derwent Abstract of FR 2694018 A.
Derwent Abstract of JP 3148210.
Derwent Abstract of DE 3901286 A.
Derwent Abstract of EP 0 315 541 A1.
Derwent Abstract of JP 62099319 A.
Derwent Abstract of HU 74489 T.
Estee Lauder "Unline Total Eyecare" Product Information.
Elizabeth Arden "Ceramide Herbal 12" Product Information.
Elizabeth Arden "Millennium Energist Emulsion Revitalisante" Product Information.
Z.A.A. Enterprises Nature'Touch "Tawas for Dry Skin" Product Information.
Revlon "Natural Honey" Product Information.
Revlon "Natural Honey Lotion" Product Information.
Docteur Payot "Creme de Ville Peaux Seches" Product Information.
Docteur Payot "Creme de Ville Toutes Peaux" Product Information.
Elizabeth Arden "Perpetual Moisture" Product Information.
Yves Saint Laurent "Visible Energie" Product Information.
Yves Rocher "Purete Originelle Masque Ananas" Product Information.
Yves Rocher "Purete Originelle Masque Peche" Product Information.
Yves Rocher A.D.N. Vegetal "Soin Eclaf Vital"Product Information.
Yves Saint Laurent "Prevention and Time Prevention Day Creme" Product Information.
Sisley "Tenseur Beaute Phytoatomatique" Product Information.
Yves Rocher Purete Originelle LaitPurete Product Information.
Yves Saint Laurent "Hydratant Absolu" Product Information.
Yves Saint Laurent "Hydra Fluid" Product Information.
Yves Rocher "Purete Originelle Gel Purete"Product Information.
Yves Rocher "Purete Originelle Lotion Purete" Product Information.
Yves Saint Laurent "Teint Spontane" Product Information.
Scholl "Softening Lotion" Product Information.

* cited by examiner

US 6,861,077 B1

USE OF PLANT EXTRACTS IN A COSMETIC COMPOSITION TO PROTECT KERATINOUS FIBERS

CROSS-REFERENCE TO RELATED APPLICATION

This application is a continuation-in-part of co-pending U.S. application Ser. No. 09/527,599, filed Mar. 17, 2000, which is hereby incorporated by reference in its entirety.

BACKGROUND OF THE INVENTION

1. Field of the Invention

The present invention is directed to a composition for keratinous fibers and to methods of treating keratinous fibers with the composition in order to provide protection from extrinsic damage and to provide improved styling properties and other qualities. For example, the inventive composition can provide protection to hair while improving combability and curl formation. More particularly, the present invention is directed to a composition comprising plant extracts that provides protection benefits to keratinous fibers, including hair, eyelashes, and eyebrows.

Keratinous fibers, especially hair, are constantly exposed to harsh extrinsic conditions such as sun, chemical damage, e.g., from detergents, bleaching, relaxing, dyeing, and permanent waving, and heat, e.g., from hair dryers or curlers. These external factors generally result in damage to the keratinous fibers. There is a need, therefore, for cosmetic products that are useful in restoring and protecting keratinous fibers from such harsh extrinsic conditions.

2. Description of the Prior Art

In this age of the immense popularity of "natural" based consumer products, specific groups of plant extracts have been identified for their "healing" or protecting properties with regard to keratinous tissue. In particular, plant extracts have been used in numerous skin care compositions such as: compositions containing carrot, tomato, tobacco, bean or potato extracts for the repair of sun damaged skin (U.S. Pat. No. 5,547,997); compositions containing actzuki bean, catechu, or avocado extracts for preventing and improving multiple skin conditions (European Patent EP965328 A1); compositions containing herbal extracts such as dill, horseradish, oats, neem, beet, broccoli, tea, pumpkin, soybean, barley, walnut, flax, ginseng, poppy, avocado, pea or sesame for the delivery of active ingredients in the form of adhesive strips which remove keratotic plugs from skin pores (U.S. Pat. No. 5,985,300); topical formulations containing orange, avocado, watermelon, banana, lemon, palm oil, or coconut oil for the treatment of redness, swelling, itching, and soreness of the skin (U.S. Pat. No. 5,932,230); skin cream compositions containing the juice of an avocado, cucumber, lemon, or weeping willow for cleansing, moisturizing, nourishing and healing the skin (U.S. Pat. No. 4,722,843); a skin moisturizing and cleansing cream comprising a mixture of a predominant amount of fresh fruit (U.S. Pat. No. 4,297,374); and skin moisturizing and sunscreen compositions containing biological extracts such as green tea extract, horsetail extract, sunflower extract, and wheat germ extract (U.S. Pat. No. 5,788,954).

The healing properties of certain plant extracts have also been used in hair care compositions such as: hair cosmetic compositions containing a plant extract chosen from bark of birch, grass of rosemary, and avocado (U.S. Pat. No. 4,839,168); compositions for treating dandruff (U.S. Pat. No. 5,053,222) and hair growth-promoting compositions (JP62099319) containing mistletoe; and compositions containing a bean extract (JP59101414) that correct damaged hair.

While popular opinion regarding some of the touted uses of plant extracts ranges from skepticism to disbelief, there appears to be a firm scientific basis for many of the assertions. For example, many plant extracts contain lectins, also referred to as agglutinins, affinitins, phytoagglutinins, phasins or protecting. These are a group of proteins or glycoproteins, of both plant and animal origin, that have specific binding affinity to sugar groups which exist in polysaccharides or glycoproteins. Not to be limited as to theory, it is believed that this binding affinity to sugars is responsible for the observed therapeutic or protective properties that make plant extracts a choice material for use in target delivery of active ingredients or therapeutic agents.

U.S. Pat. No. 4,217,341, for example, discloses compositions containing lectins which bind and agglutinate dental-plaque producing bacteria, thereby inhibiting the adherence of said bacteria to smooth surfaces such as teeth surfaces. Similarly, U.S. Pat. No. 5,607,679 discloses a method of treatment of a skin disease by binding lectins to a sialylated TF antigen of the skin. The specific affinity of lectins for sugars is also taught in U.S. Pat. No. 5,510,120 and EP0481701 B1 where the lectin is covalently bound to a liposome which also contains an active ingredient. Thus the active is delivered to the specific site desired.

Plant extracts and lectins are also used in the characterization of carbohydrates because of their ability to bind to some sugar molecules and moieties, and their ability to cause cell agglutination by binding to the glycoproteins located in the cell membrane. The nature of the binding sites can be determined by the hapten-inhibition test. See Kornfeld, S. and Kornfeld, R., *Lectins in the Study of Glycoproteins* (1978). In this assay, various carbohydrates are tested for their ability to inhibit the lectin-induced agglutination of the test cells. It has been shown that various lectins react with a number of different carbohydrates, both simple and complex sugars. See Kornfeld, S. and Kornfeld, R., *Glycoproteins of Blood Cells and Plasma* (1971). In the majority of cases, the affinity of lectins to complex oligosaccharides is much greater than that to simple sugars. Among the lectins shown to have carbohydrate-binding sites of the complex type are the lectins from potato (*Solanum tuberosum*). Allen, A. K. and Neuberger, A., *J. Biochem.* 135, 307–314 (1973). *Solanum tuberosum* agglutinin (STA), which has an affinity for N-acetyl-$\beta$-D-glucosamine oligomers, is a glycoprotein containing approximately equivalent amounts of protein and carbohydrate.

SUMMARY OF THE INVENTION

In light of the useful properties of plant extracts discussed above, and in order to meet the public's demand for consumer products based on natural ingredients, there is a need for more cosmetic products that utilize the binding properties of plant extracts and can be useful in restoring and protecting keratinous fibers.

To achieve these and other advantages, and in accordance with the purpose of the invention as embodied and broadly described herein, the present invention, in one aspect, provides a method of protecting keratinous fiber from extrinsic damage, e.g., protein loss caused by exposure to heat, chemicals, etc., by applying to keratinous fiber a composition that contains at least one plant extract chosen from potato extract, mistletoe extract, avocado extract, wheat germ extract, and willowherb extract. The present invention also contemplates a method of improving combability and/or a method of improving curl formation of keratinous fibers by applying to the keratinous fibers a composition containing at least one plant extract.

In another embodiment, the present invention is drawn to a composition for the treatment or protection of keratinous fiber, the composition comprising at least one plant extract chosen from willow herb extract.

Additional objects and advantages of the invention will be set forth in part in the description which follows, and in part will be apparent from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention as claimed.

DETAILED DESCRIPTION OF THE INVENTION

Figure 1:
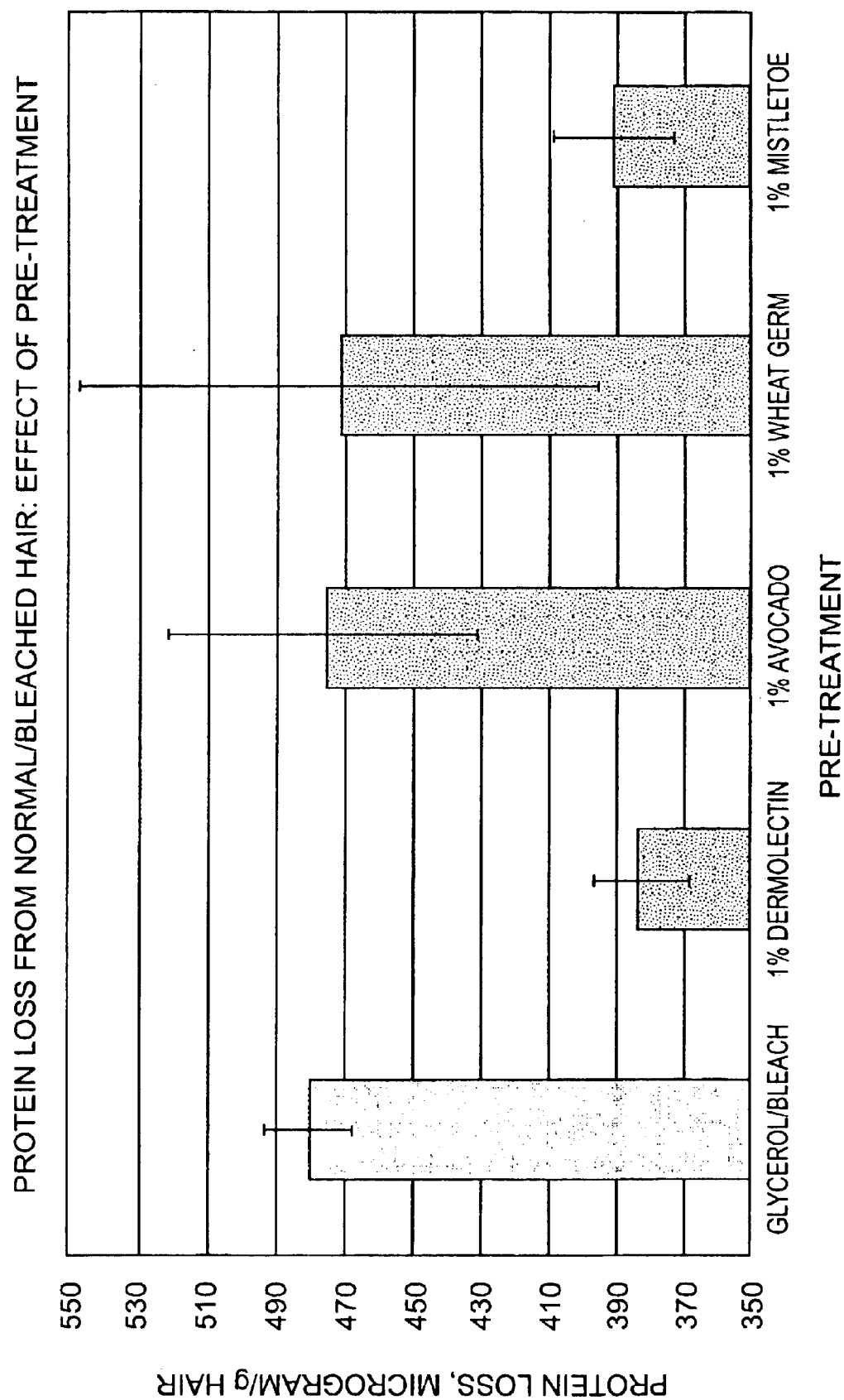
FIG. 1: The evaluation of plant extracts for the protection of hair using the protein loss test on normal/bleached hair.

Reference will now be made in detail to the presently preferred embodiments of the present invention. The invention, in one aspect, provides a method of protecting keratinous fiber from extrinsic damage by applying to keratinous fiber a composition that contains at least one plant extract chosen from potato extract, mistletoe extract, avocado extract, wheat germ extract, and willowherb extract. Extrinsic damage is damage that is caused by conditions such as sun, chemical damage, e.g., from detergents, bleaching, relaxing, dyeing, and permanent waving, and heat, e.g., from hair dryers or curlers. Examples of keratinous fiber include hair, eyelashes, and eyebrows. The composition may further comprise at least one sugar.

The present invention also contemplates a method of improving combability and/or a method of improving curl formation of keratinous fibers by applying to the keratinous fibers a composition comprising at least one plant extract. The composition may further comprise at least one sugar.

Plant extracts are known to bind to carbohydrate moieties, including the carbohydrate moieties of glycoproteins on the surface of cells. Therefore, it naturally follows that plant extracts should bind to keratinous fiber, which contains a number of sugars and carbohydrate moieties. It was unexpectedly discovered by the present inventors, however, that in addition to binding to keratinous fiber, plant extracts and plant extract-like materials provide protection from extrinsic conditions to the keratinous fiber and also impart other desired benefits to keratinous fiber. Even more surprising was the ability of plant extracts to provide greater protection to keratinous fiber, especially hair, that has already been damaged by extrinsic conditions as compared to non-damaged hair.

For example, human hair contains a number of sugars or carbohydrate moieties, as summarized in Table 1 below. See Mathews, et al., Cosm. Technology 10 (1981). One such carbohydrate moiety is N-acetylneuraminic acid (NANA), which is found on the surface of the hair fiber. The presence of NANA in human hair can be observed by extracting the hair with acid under mild hydrolysis conditions. NANA is the most common member of the group of sialic acids, which are encountered in nature as terminal residues in the oligosaccharide moieties of glycoproteins. Thus, NANA indicates the presence of glycoproteins in hair.

TABLE 1

Monosaccharide content in normal hair

| Monosaccharide | $\mu$mole/g hair |
| --- | --- |
| Glucosamine | 1.01 ± 0.09 |
| Galactosamine | 0.26 ± 0.05 |
| Galactose | 0.46 ± 0.37 |
| Glucose | 5.73 ± 1.43 |
| Mannose | 1.02 ± 0.37 |
| Xylose | 0.56 ± 0.14 |
| Fucose | 0.14 ± 0.05 |
| Hexuronic acid | 8.53 ± 0.05 |
| Sialic acids | 0.37 ± 0.01 |

As the terminal residue, NANA is the first constituent exposed to the attack during various treatments applied to hair. Preliminary studies on the NANA distribution within the hair fiber, indicate that as much as 25% to 30% of the total NANA content may reside close to the hair surface. Therefore, it is not surprising that the amount of NANA in hair decreases after water extraction, and is drastically reduced after acid extraction and after severe bleaching. In other words, the amount of NANA in keratinous fibers decreases as the fibers are damaged by extrinsic conditions such as water, chemical damage and heat. These treatments can be chemically non-aggressive (water; surfactants), as well as aggressive (permanent waving, often referred to as a "perm"; oxidative color/bleach; alkaline hair straightening). While detailed information on the function of NANA and glycoproteins in human hair is still lacking, it is known from other sources that the removal of one NANA residue from the oligosaccharide chain can change physical and biochemical properties of biomolecules. See Sharon, N., and Lis, H., The Proteins Vol. V, 1–145 (H. Neurath and R. L. Hill eds. Academic Press, NY) (1982).

Therefore, not to be limited as to theory, using plant extracts to protect terminal groups, such as NANA, during chemical attacks may result in the hair being protected during aggressive treatments. By the same token, plant extracts binding to NANA and the oligosaccharide chains of hair could protect normal and damaged hair against protein loss during non-aggressive treatments. Similarly, a carbohydrate moiety that is found in the skin and other keratinous tissue, e.g., glycosaminoglucans (GAG's), may enable plant extracts to provide other keratinous tissue with the same protection as found for hair.

Thus, plant extracts have been shown to bind to keratinous fiber and impart protective effects to the fiber from damage by extrinsic conditions. Plant extracts also condition the surface of the fiber and retain the integrity of keratinous fibers by reducing cuticle loss. In addition to protecting keratinous fiber, plant extracts improve the combability and the curl formation of keratinous fibers.

Any plant extract that binds to carbohydrate moieties or sugars may be useful in the practice of the invention. A plant extract useful in the methods of the invention may also be any plant extract that protects keratinous fibers from protein loss. The skilled artisan may determine by routine experimentation if a plant extract binds to carbohydrate moieties or protects keratinous fibers from protein loss depending on the application envisaged. Routine experiments for determining if a plant extract may be useful in the practice of the invention include column chromatography, as described in Example 1, which determines the binding of a plant extract to a carbohydrate moiety; the protein loss test, as described in Example 2, which determines whether a plant extract protects keratinous fibers from protein loss; and the combability test, as described in Example 3, which compares the increase in wet combing work caused by extrinsic conditions for hair treated with a plant extract versus untreated hair. However, a positive result in any or all of the tests provided is not necessarily required for a plant extract to be useful in the compositions and methods of the invention The combability test (See Garcia, M. L., and Diaz, J., *J. Soc. Cosmet. Chem.* 27, 370–398 (1976)), is known in the art to correlate well to the amount of protection from exposure to extrinsic conditions that is afforded hair by a composition. Wet combing work of normal hair is determined prior to treatment. The hair is then divided into two groups and treated, one group with the plant extract and the other group with control solutions. Following treatment, the hair is exposed to harsh extrinsic conditions such as heating. The increase in work or force required to comb wet hair is compared for the exposed hair treated with the plant extract versus the exposed hair treated with the controls.

Preferred plant extracts of the present invention include, but are not limited to, willowherb extract; potato extracts such as Dermolectine® and Capilectine®; mistletoe extract; avocado extract; wheat germ extract; kidney bean extract; other vegetable extracts such as carrot, soybean, oat, beet, cucumber, broccoli, pumpkin and tomato extract; tobacco extract; other herbal extracts such as dill, horseradish, weeping willow, ginseng, poppy, or sesame; other fruit extracts such as orange, lemon, watermelon, banana, and coconut. Plant extracts are generally supplied in water or glycerol solutions containing, for example, in the case of Dermolectine® 60% glycerol, but it is possible that they may be obtained in more concentrated form. Additionally, many suppliers do not provide the percent active ingredient for commercially available plant extracts.

In a further preferred embodiment, the plant extracts of the present invention are chosen from plant extracts containing lectins. Lectins can be extracted from a variety of plant or animal materials and can be categorized by their affinity to a particular sugar or sugar complex. Lectins useful in the practice of the invention include, but are not limited to: *Solanum tuberosum L..* (potato extract), which may be purified by affinity chromatography and is commercially available from SEDERMA, Inc. (France) as Dermolectine® (700 mg/100 g actives concentration) and Capilectine® (500 mg/100 g actives concentration), ALBAN MULLER, Int. (France) and VEGETECH (CA); *Lycopersicon esculentum* (tomato extract); *Agaricus bisporus* (mushroom extract); *Arachis hypogea* (peanut extract); *Bauhinia pupurea* (camel's foot tree or seed extract); *Anguilla anguilla* (fresh water eel extract); *Tetragonolobus purpureas* (winged pea extract); *Ulex europaeus* (gorse or furze extract); *Lathyrus odoratus* (sweet pea extract); *Lens culinaris* (lentil extract) or *Pisum sativum* (pea extract); and agglutinins from *Glycine max* (soybean extract), *Helix aspersa* (garden snail extract) or *Helix pomatia* (roman or edible snail extract).

The compositions of the present invention may also contain at least one sugar. Compositions comprising mixtures of one or more plant extracts are within the practice of the invention, as are compositions comprising mixtures of one or more plant extracts and one or more sugars.

The sugars useful in the present invention may be any sugar, carbohydrate or carbohydrate moiety. In a preferred embodiment, the sugars may be chosen from monosaccharides, which include, but are not limited to, any three to seven carbon sugars such as pentoses, e.g., ribose, arabinose, xylose, lyxose, ribulose, and xylulose, and hexoses, e.g., allose, altrose, glucose, mannose, gulose, idose, galactose, talose, sorbose, psicose, fructose, and tagatose; disaccharides (which are saccharides that hydrolyze into two monosaccharides) such as maltose, sucrose, cellobiose, trehalose and lactose; and polysaccharides (which are saccharides that hydrolyze into more than two monosaccharides) such as starch, dextrins, cellulose and glycogen. In another embodiment, the sugars of the invention are chosen from aldoses and ketoses.

In a preferred embodiment, the mixture of at least one plant extract and at least one sugar is chosen from mixtures of potato extracts such as Dermolectine® and/or Capilectine® and one or more sugars chosen from sorbose, sucrose and trehalose; kidney bean extract and sucrose; and willowherb extract and sucrose.

In a preferred embodiment, a plant extract or mixture of plant extracts is present in the compositions of the present invention in an amount ranging from 0.01% to 5.0% relative to the total weight of the composition. When a sugar or mixture of sugars is present in the compositions of the present invention, it is preferably present in an amount ranging from 0.001% to 3.0% relative to the total weight of the composition. These ranges are based on a commercially available plant extract composition, which is approximately 60% glycerol. The preferred ranges of plant extract present in the compositions of the present invention may vary depending on the percent active ingredient of the plant extracts as supplied commercially.

The compositions of the present invention may be in the form of a liquid, oil, paste, stick, dispersion, emulsion, lotion, gel, or cream. The compositions of the present invention may also be provided as one-part compositions comprising the plant extract or mixture of plant extracts and, optionally, the sugar or mixture or sugars or in the form of a multicomponent treatment or kit. The multicomponent kit may comprise one component that contains a plant extract and another component that optionally contains a sugar. The skilled artisan, based on the stability of the composition and the application envisaged, will be able to determine how the composition and/or multicomponent compositions should be stored and mixed.

In another embodiment, the present invention is drawn to a composition for the treatment or protection of keratinous fiber, the composition comprising willowherb extract. The composition may further comprise at least one sugar.

The invention will be illustrated by, but is not intended to be limited to, the following examples.

EXAMPLE 1

A Test to Determine the Binding of a Plant Extract to a Carbohydrate Moiety

A screening test to determine the applicability of a plant extract for use in the compositions of the present invention was carried out. Since any plant extract that binds to carbohydrate moieties or sugars may be useful in the practice of the invention, the skilled artisan may use column chromatography or HPLC to quickly determine the binding properties of a plant extract to a specific carbohydrate and therefore the possible utility of that plant extract for the application envisaged.

HPLC experiments were performed as shown in Table 4 below. A cation exchange chromatographic column that will not retain NANA but will retain or slow the elution of a NANA/plant extract complex was chosen, in this case a NANA/Dermolectine® complex. The amount of NANA recovered following HPLC with the control solution (glycerol was chosen as a control because the Dermolectine® solution contained 60% glycerol), as calculated from NANA's absorption at 200 nm, was then compared to the amount of NANA recovered following HPLC with a solution containing the potato extract, Dermolectine®.

NANA in the glycerol control solution was not retained by the column during HPLC and 100% of the NANA was recovered at a time A. Therefore, any NANA from the NANA/Dermolectine® solutions passed through the column that was not recovered at time A was due to an interaction between NANA and the Dermolectine®. As shown in Table 4, below, the lower amounts of NANA recovered following HPLC demonstrated that Dermolectine® is capable of binding NANA.

TABLE 4

Effect of Dermolectin ® on NANA Determination by HPLC
(200 nm Detection)

| Solution | % NANA Recovered |
| --- | --- |
| NANA in 60% Glycerol*/0.1 N $H_2SO_4$ | 100 |
| NANA in 60% Glycerol*/0.1 N $H_2SO_4$, 1 h at 80° C. | 100 |
| NANA in 100% Dermolectine ®/0.1 N $H_2SO_4$ | 80 |
| NANA in 100% Dermolectine ®/0.1 N $H_2SO_4$, 1 h at 80° C. | 66 |

*Dermolectine ® contains 60% glycerol.

EXAMPLE 2

A Test to Determine the Protection of Keratinous Fibers from Protein Loss by a Plant Extract Another screening test to determine the applicability of a plant extract for use in the compositions of the present invention was carried out. A plant extract useful in the compositions of the invention may also be any plant extract that protects keratinous fibers from protein loss. The skilled artisan may determine by the protein loss test, whether a plant extract protects keratinous fibers from protein loss.

The effect of the potato extracts, Dermolectine® and Capilectine®, respectively, on the protein loss from keratinous fibers in water was tested against the control, glycerol. Each of the solutions of Table 5 below, was applied to a swatch of bleached hair for 5 minutes at room temperature (ratio of hair:liquid=1:10, w/w). The hair swatches were then rinsed with tepid water for one minute, air-dried, and then each swatch was placed in a separate 50 ml Erlenmeyer flask and deionized water was added at a ratio of hair:water= 1:15, w/w. The hair samples were shaken in a Gyrotory Water Bath Shaker Model G76 (New Brunswick Scientific Co.) for 1 hour at room temperature.

The protein content in each water sample was determined by the Lowry technique. See Sandhu, S. S., and Robbins, C. R., J. Soc. Cosmet. Chem., 44, 163–175 (1993). As shown in Table 5, the protein loss from the hair pre-treated with 1% solutions of Dermolectine® and Capilectine® was significantly lower than that from the hair pre-treated with the glycerol solution.

TABLE 5

Protein Loss in Water from Bleached Hair.
Effect of One Pre-treatment

| Treatment Solution | Protein loss, mg/g hair |
| --- | --- |
| No treatment | 3.05 ± 0.02 |
| 0.6% Glycerol - Control | 2.56 ± 0.06 |
| 1% Capilectine ® | 1.76 ± 0.04 |
| 1% Dermolectine ® | 2.09 ± 0.06 |

In another experiment, 1% solutions of different potato extracts were tested for their capacity to protect bleached hair from protein loss. The effect of the glycerol-containing extracts Dermolectine®, Capilectine®, and Potato HS®, was compared to that of 0.6% glycerol, while the glycerol-free raw materials, Potato Peel Extract and Potato Extract, (VEGETECH), were tested against water. See Table 6 below.

Swatches of bleached hair were treated with the above solutions for 5 minutes at room temperature, and rinsed with tepid water for one minute. The treatments were repeated five times. The shaking-in-water procedure was conducted as described above. In all cases, the protein loss from the bleached hair treated with the potato extracts was significantly lower than that from the corresponding control swatches (See Table 6).

TABLE 6

Protein Loss in Water from Bleached Hair.
Effect of Five Pre-Treatments

| Treatment Solution | Protein loss, mg/g hair |
| --- | --- |
| I. Glycerol Containing Solutions | |
| 1.0% Glycerol-Control | 0.75 ± 0.09 |
| 1% Capilectine ® | 0.55 ± 0.09 |
| 1% Dermotectine ® | 0.61 ± 0.05 |
| 1% Potato HS ® | 0.44 ± 0.05 |
| II. Glycerol-Free Solutions | |
| Water treatment-Control | 0.97 ± 0.11 |
| 1% Potato Peel Extract | 0.61 ± 0.08 |
| 1% Potato Extract | 0.76 ± 0.05 |

EXAMPLE 3

Protection of Normal Hair by Plant Extracts During Bleaching

The combability test was used to determine the amount of protection from extrinsic conditions afforded hair by a composition of the invention. The wet combing force of normal brown hair was determined prior to further treatment. See Garcia, M. L., and Diaz, J., J. Soc. Cosmet. Chem. 27,370398 (1976). Next, solutions of the potato extracts, Dermolectine® and Potato HS® respectively, each at concentrations of 0.5%, 1.0%, and 3% by weight, were applied to the hair for 5 minutes at room temperature (hair:solution= 1:10, w/w). Dermolectine® and Potato HS® each contain 60–80% glycerol, therefore these potato extracts were tested against 3% glycerol solutions (control). The treatment was repeated three times, with the hair being rinsed and air-dried between each application. The pre-treated normal hair was then equilibrated under room conditions for 24 hours and bleached (30 minutes at room temperature; 12% $H_2O_2$, pH 9.7 adjusted with ammonia). The bleached hair was tested for the increase in wet combing force as compared to the initial wet combing force for normal brown hair before treatment and bleaching. All tests were performed in duplicate.

As shown below in table 7, the increase in the wet combing force for hair pre-treated with Dermolectine® or Potato HS® solutions was significantly lower than that observed for hair pre-treated with the glycerol solution.

TABLE 7

Wet Combing of Bleached Hair: Effect of Pre-Bleach Treatment. (Tests performed in duplicate; 10 comb strokes per test)

| Treatment | Increase in wet combing energy, % |
|---|---|
| 3% Glycerol | 178.9 ± 12.6 |
| 0.5% Potato HS ® | 109.7 ± 2.1 |
| 1.0% Potato HS ® | 109.8 ± 3.7 |
| 3.0% Potato HS ® | 73.8 ± 11.3 |
| 0.5% Dermolectine ® | 106.6 ± 3.41 |
| 1.0% Dermolectine ® | 113.7 ± 6.21 |
| 3.0% Dermolectine ® | 104.1 ± 9.96 |

EXAMPLE 4

Improved Combing of Bleached Hair Treated with Plant Extracts

The combability or wet combing force for bleached hair was determined before and after treatment with potato extract. Bleached hair was treated with a solution of 1% of the potato extract, Capilectine®, while another sample of bleached hair was treated with a solution of 0.6% glycerol. All samples were treated for 5 minutes at room temperature at a hair:liquid ratio of 1:10 (w/w) and then rinsed for 3 minutes with tepid water. The wet combing force after the Capilectine® application was lessened, indicating that the application improved the combability by 45%, while there were no significant changes after the glycerol treatment (Table 8).

TABLE 8

Improvement in Wet Combing of Bleached Hair (Tests performed in duplicate; 10 comb strokes per test)

| Treatment | Percent Improvement in wet combing energy, % |
|---|---|
| 0.6% Glycerol | no change |
| 1.0% Capilectine | 45.2 |

EXAMPLE 5

Improved Curl Formation in the Permanent Waving of Normal and Tinted Hair Treated with Plant Extract The curl formation in the permanent waving of 12 fiber swatches of normal brown hair and normal brown hair tinted with ColorGel® 6RO (Redken) using 20 volume of $H_2O_2$ was measured. The swatches ($I_o$ (average initial length)= 12.5 cm) were wound on perm rods (7.5 mm diameter), 6 rods per test (n=6). Each of three groups of swatches was saturated with one of the following pre-treatments: a) water; b) 0.6% glycerol; c) 1% Dermolectine®, respectively, at a ratio of 2 ml per rod; and maintained for 5 min at room temperature. Next, the rods were blotted with paper-towel, and the permanent waving reforming lotion was applied (10% Thioglycolic acid (TGA), 1% Betaine, pH 9.01, $NH_4OH$; 2 ml per rod). The hair was processed for 30 minutes at room temperature; rinsed in deionized water (100 mL/6 rods; 5 minutes); neutralized with 2% $H_2O_2$, pH 3 (5 minutes; 2 ml/rod); and again rinsed with deionized water (100 mL/6 rods; 5 minutes). The rods were blotted with a paper towel, the hair was taken off the rods, and the diameter and the length of the wet curl were measured. The length of the dry curl of the swatches was measured after drying in a vertical position on the board.

As shown in Table 9 below, the wet and the dry curl length of the hair pre-treated with 1% Dermolectine® was significantly lower, as compared to the hair pre-treated with water. There was no significant difference in the curl formation between the water- and the glycerol-treated hair.

TABLE 9

Improvement in Perm Efficiency: Effect of Pre-Treatment

| Hair type/ Treatment | Avg. Wet curl length, cm $I_o$ = 12.5 cm n = 6 | Avg. Dry curl length, cm $I_o$ = 12.5 cm n = 6 |
|---|---|---|
| Normal Brown Hair: | | |
| Water | 5.20 ± 0.19 | 6.60 ± 0.18 |
| 0.6% Glycerol | 5.32 ± 0.40 | 6.83 ± 0.42 |
| 1% Dermolectine ® | 4.80 ± 0.32 | 6.02 ± 0.19 |
| Brown Hair Tinted with ColorGel ® 6RO: | | |
| Water | 6.03 ± 0.32 | 6.95 ± 0.35 |
| 0.6% Glycerol | 6.05 ± 0.33 | 7.08 ± 0.27 |
| 1% Dermolectine ® | 5.08 ± 0.25 | 6.28 ± 0.31 |

EXAMPLE 6

Protection of Normal Hair with Plant Extracts

Swatches of normal brown hair were treated with one of the following 1% solutions of: Dermolectine®, avocado extract (Active Organics), Mistletoe Extract (Active Organics), and Wheat Germ Extract (Active Organics). Since all of the plant extracts contained 60 to 80% glycerol, control swatches of hair were treated with water and 1% glycerol, respectively. The hair was then bleached with 12% $H_2O_2$, pH 8.8 ($NH_4OH$) for 20 minutes at room temperature. There was no significant difference in the lift of color between the extract treated and water treated swatches.

The hair was digested in 6N HCL (110° C., 24 hours) and analyzed for cysteic acid using a Beckman System 6300 High Performance Analyzer. The cysteic acid content is another way to measure the amount of damage to hair fibers caused by bleaching. The higher the cysteic acid content, the more damage done to the hair. As shown in Table 10 below, while all of the plant extracts tested protected hair from loss of NANA relative to water and glycerol, there was no appreciable difference in the cysteic acid content of hair pretreated by plant extract.

The hair was also analyzed for protein loss in water as described above. Table 10, below, and FIG. 1, attached, show that mistletoe extract and Dermolectine® provided protection against protein loss at these low concentrations. While no appreciable protection against protein loss was observed for wheat germ extract or Avocado extract at these concentrations, protection against protein loss may be observable at higher concentrations of plant extract.

Finally, the hair was analyzed for NANA content. NANA content was measured by the following procedure. The hair was digested with papain/dithiotreitol, lyophilized, and reconstituted with 0.2 N $H_2SO_4$. The hair was then hydrolyzed at 80° C. for 1 hour, derivatized with the fluorescent probe, 1,2-diamino-4,5-methlenedioxybenzene, and analyzed for NANA content by reverse-phase HPLC. As shown in Table 10, all of the plant extracts protected the hair from loss of NANA during bleaching, which indicates protection of hair surface glycoproteins.

TABLE 10

Protection of Hair with Plant Extracts

| Hair/Treatment | NANA, nmole/g hair | Cysteic acid, Mole % | Protein loss, µg/g hair |
|---|---|---|---|
| Normal Hair | 619 ± 13 | 0.5 ± 0.1 | 306 ± 3 |
| Bleached hair, pretreated with: | | | |
| Water | 409 ± 71 | 1.8 ± 0.2 | 410 ± 60 |
| 1.0% Glycerol - Control | 485 | 1.9 ± 0.2 | 481 ± 13 |
| 1% Wheat Germ | 500 ± 5 | 1.8 ± 0.1 | 471 ± 76 |
| 1% Mistletoe | 506 ± 43 | 2.2 ± 0.1 | 390 ± 18 |
| 1% Dermolectine ® | 560 ± 55 | 1.8 ± 0.1 | 380 ± 14 |
| 1% Avocado | 585 ± 28 | 1.9 ± 0.1 | 476 ± 45 |

A similar experiment was performed using hair that was bleached one time (1x). Swatches of bleached hair were treated by one of the following procedures:

a) 0.5% potato extract (VEGETECH) solution was applied for 5 minutes at room temperature, rinsed under tap water, air-dried, and equilibrated for 24 hours at room conditions before bleaching;

b) 2.0% potato extract (VEGETECH) solution was applied following the procedure set forth in (a);

c) 0.5% potato extract (VEGETECH) solution was applied for 5 minutes at room temperature, blot-dried with a paper towel, air-dried, and equilibrated for 24 hours at room conditions before bleaching; and d) 1.0% potato extract (VEGETECH) solution was applied following procedure (c). The potato extracts did not contain glycols, therefore, water was used as a control treatment.

The bleached hair was then bleached again with 12% $H_2O_2$, pH 8.8 ($NH_4OH$) for 20 minutes at room temperature. There was no significant difference in the lift of color between the extract-treated and water-treated swatches. The hair was analyzed for cysteic acid and protein loss in water as described above.

Figure 2:
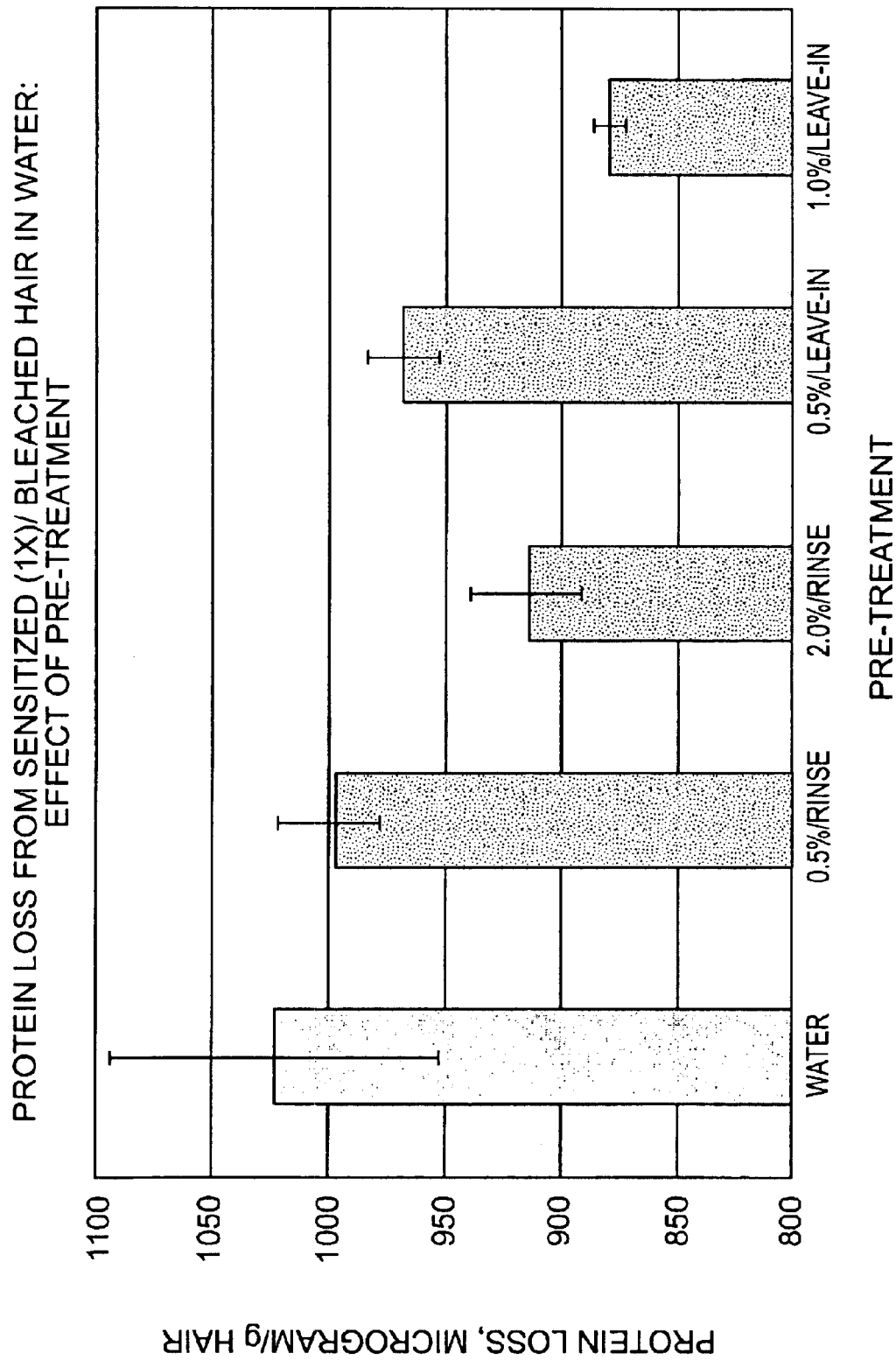
FIG. 2: The evaluation of plant extracts for the protection of hair using the protein loss test on bleached hair.

As shown in Table 11, each of the plant extract solutions protected the hair from cysteic acid formation. In addition, as shown in Table 11 and FIG. 2, each of the plant extract solutions protected the hair from protein loss. A concentration dependence was also observed with regard to the ability of a plant extract to protect hair from protein loss.

TABLE 11

Protection of Bleached Hair with Plant Extracts

| Hair/Treatment | Cysteic acid, Mole % | Protein loss, µg/g hair |
|---|---|---|
| Bleached Hair, 1X | 2.9 ± 0.1 | 360 ± 2 |
| Bleached Hair after Second Bleaching (2X), pretreated with Potato Extract: | | |
| Water (control) | 4.4 ± 0.1 | 1023 ± 70 |
| 0.5% Extract, rinsed | 3.8 ± 0.1 | 1000 ± 21 |
| 2.0% Extract, rinsed | 3.9 ± 0.1 | 914 ± 23 |
| 0.5% Extract, left-in | 3.7 ± 0.1 | 916 ± 15 |
| 1.0% Extract, left-in | 3.6 ± 0.1 | 878 ± 5 |

EXAMPLE 7

Protecting Hair Using a Plant Extract/Sugar Mixture

The combability test was used to demonstrate the effective protection from extrinsic conditions, such as heat, afforded hair by a composition of the invention. The wet combing force of bleached hair was determined prior to further treatment. Next, hair swatches were treated with one of the following solutions:

a) water (control);
b) sugar solution;
c) willowherb solution; and
e) willowherb and sugar mixture.

The solutions were applied to the hair for 5 minutes at room temperature (hair:solution ratio=1:10, w/w). The treatment was repeated six times, with the hair being rinsed and subjected to heating cycles between each treatment. See McMullen, R. and Jachowicz, J., *J. Cosmet. Sci.,* 49, 223–244 (1998). The bleached hair was tested for the increase in wet combing force as compared to the initial wet combing force of the bleached hair before treatment and heating to determine the efficacy of the treatments against heat exposure.

Figure 3:
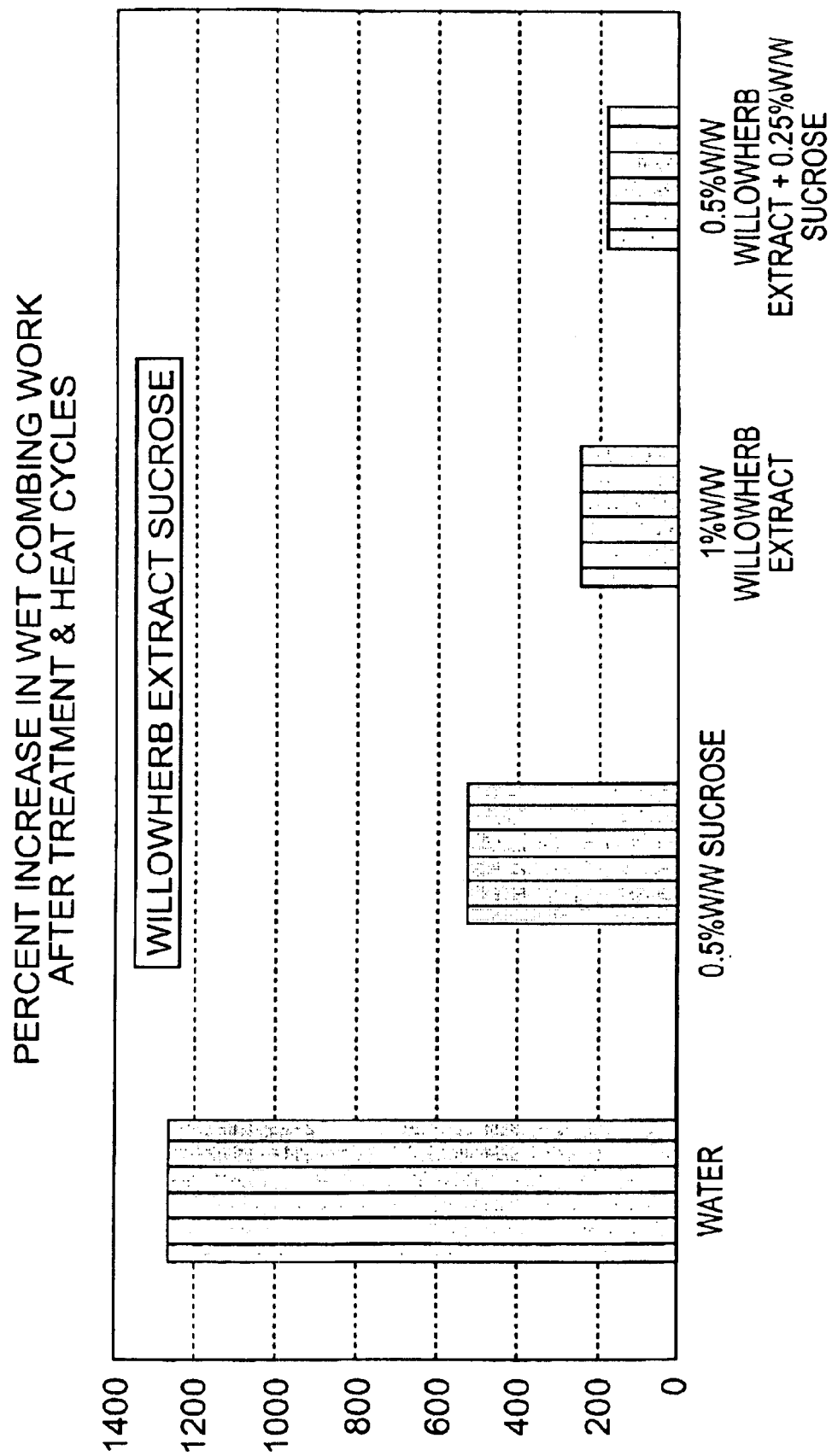
FIG. 3: Compositions containing willowherb extract and mixtures of willowherb extract and sucrose are evaluated for their ability to protect hair by measuring the increase in wet combing work.

FIG. 3 shows a reduction in percent increase in wet combing work. This indicates that there was a effective protection of hair from heat cycles using willowherb extract or a willowherb extract/sucrose mixture at the concentrations shown.

It will be apparent to those skilled in the art that various modifications and variations can be made in the compositions and methods of the present invention without departing from the spirit or scope of the invention. Thus, it is intended that the present description cover the modifications and variations of this invention provided that they come within the scope of the appended claims and their equivalents.

What is claimed is:

1. A method of protecting keratinous fiber from extrinsic damage comprising
applying to said keratinous fiber a composition comprising an effective amount of at least one plant extract chosen from willowherb extract.

2. A method of protecting keratinous fiber from extrinsic damage according to claim 1, wherein said composition further comprises at least one sugar.

3. A method of protecting keratinous fiber from extrinsic damage according to claim 2, wherein said sugar is chosen from monosaccharides, disaccharides and polysaccharides.

4. A method of protecting keratinous fiber from extrinsic damage according to claim 3, wherein said monosaccharides are chosen from pentoses and hexoses.

5. A method of protecting keratinous fiber from extrinsic damage according to claim 4, wherein said pentoses are chosen from ribose, arabinose, xylose, lyxose, ribulose, and xylulose.

6. A method of protecting keratinous fiber from extrinsic damage according to claim 4, wherein said hexoses are chosen from allose, altrose, glucose, mannose, gulose, idose, galactose, talose, sorbose, psicose, fructose, and tagatose.

7. A method of protecting keratinous fiber from extrinsic damage according to claim 3, wherein said disaccharides are chosen from maltose, sucrose, cellobiose, trehalose and lactose.

8. A method of protecting keratinous fiber from extrinsic damage according to claim 3, wherein said polysaccharides are chosen from starches, dextrins, celluloses and glycogens.

9. A method of protecting keratinous fiber from extrinsic damage according to claim 2, wherein said sugar is sucrose and said plant extract is willowherb extract.

10. A method of protecting keratinous fiber form extrinsic damage according to claim 1, wherein said composition is in the form of a liquid, oil, paste, stick, dispersion, emulsion, lotion, gel, or cream.

11. A method of protecting keratinous fiber from extrinsic damage according to claim 1, wherein said keratinous fiber is chosen from hair, eyelashes, and eyebrows.

12. A method of protecting keratinous fiber from extrinsic damage according to claim 1, wherein said at least one plant extract is present in said composition at a concentration ranging from 0.01% to 5.0% relative to the total weight of the composition.

13. A method of protecting keratinous fiber from extrinsic damage according to claim 2, wherein said at least one sugar is present in said composition at a concentration ranging from 0.001% to 3.0% relative to the total weight of the composition.

* * * * *